United States Patent [19]

Arhancet et al.

[11] Patent Number: 5,510,547
[45] Date of Patent: Apr. 23, 1996

[54] METHODS FOR INHIBITING VINYL AROMATIC MONOMER POLYMERIZATION

[75] Inventors: Graciela B. Arhancet, Katy; Inge K. Henrici, Spring, both of Tex.

[73] Assignee: Betz Laboratories, Inc., Trevose, Pa.

[21] Appl. No.: 383,159

[22] Filed: Feb. 3, 1995

Related U.S. Application Data

[63] Continuation-in-part of Ser. No. 118,075, Sep. 8, 1993, Pat. No. 5,396,004, which is a continuation-in-part of Ser. No. 964,321, Oct. 21, 1992, abandoned.

[51] Int. Cl.$^6$ ...................................................... C07C 7/20
[52] U.S. Cl. ............... 585/5; 585/3; 585/4; 208/48 AA; 252/402; 252/405; 203/8; 203/9
[58] Field of Search .................. 585/3, 5, 4; 258/48 AA; 252/402, 405; 203/8, 9

[56] References Cited

U.S. PATENT DOCUMENTS

| | | | |
|---|---|---|---|
| 4,105,506 | 8/1978 | Watson | 203/9 |
| 4,466,905 | 8/1984 | Butler et al. | 252/403 |
| 4,720,566 | 1/1988 | Martin | 558/306 |
| 4,774,374 | 9/1988 | Abruscato et al. | 252/402 |
| 5,396,004 | 3/1995 | Arhancet et al. | 585/3 |
| 5,396,005 | 3/1995 | Arhancet | 585/5 |
| 5,416,258 | 5/1995 | Arhancet et al. | 585/601 |

*Primary Examiner*—Anthony McFarland
*Attorney, Agent, or Firm*—Alexander D. Ricci; Philip H. Von Neida

[57] ABSTRACT

Methods for inhibiting the polymerization of vinyl aromatic monomers in oxygen-free processing systems are disclosed. The methods comprise adding from 1 to 10,000 parts of a combination of a hydroxylamine compound and a phenylenediamine compound to the vinyl aromatic monomer.

8 Claims, No Drawings

METHODS FOR INHIBITING VINYL AROMATIC MONOMER POLYMERIZATION

This is a continuation-in-part of Ser. No. 08/118,075, filed Sep. 8, 1993, now U.S. Pat. No. 5,396,002, which is a continuation-in-part of Ser. No. 07/964,321, filed Oct. 21, 1992, abandoned.

FIELD OF THE INVENTION

The present invention relates to methods for inhibiting the undesirable polymerization of vinyl aromatic monomer compounds.

BACKGROUND OF THE INVENTION

Polystyrene is a thermoplastic with many desirable characteristics. It is clear, transparent, readily colored and easily fabricated. The family of styrene polymers includes polystyrene itself, copolymers of styrene with other vinyl monomers, polymers of derivatives of styrene and mixtures of polystyrene and styrene-containing copolymers with elastomers. Pure polystyrene is glass-like, transparent, hard, and rather brittle.

ABS (acrylonitrile, butadiene, styrene) and SAN (styrene, acrylonitrile) resins have enjoyed tremendous commercial popularity for many years as durable, temperature and solvent resistant elastomers. On the other hand, styrene plastics are commonly used for packaging, including foams and films, coatings, in appliance fabrication, for housewares and toys, lighting fixtures and in construction materials.

Common industrial methods for producing vinyl aromatic monomers, such as styrene, include a variety of purification processes, the most common one being distillation. It is well known that vinyl aromatic monomers readily polymerize when heated and that rate of polymerization increases rapidly as the temperature increases. Thermal polymerization during distillation results not only in loss of product, but it could render the finished monomer unsuitable for using without further treatment.

To prevent polymerization of vinyl aromatic monomers under distillation conditions, various inhibitor compositions have been employed. Unfortunately, although several compounds are effective against vinyl aromatic monomer polymerization under storage conditions, only some of these compounds have proved to be effective against polymerization under distillation conditions.

SUMMARY OF THE INVENTION

The present invention relates to methods for inhibiting polymerization of vinyl aromatic monomers during monomer processing conditions such as distillation of the vinyl aromatic monomers.

The methods of the present invention provide for adding a combination of a phenylenediamine compound and a hydroxylamine compound to the vinyl aromatic monomer undergoing processing. The combination is particularly effective at inhibiting polymerization of styrene during its distillation under oxygen-free conditions.

DESCRIPTION OF THE RELATED ART

Dinitrophenol compounds are generally used commercially to inhibit polymerization of vinyl aromatic monomers. U.S. Pat. No. 4,105,506, Watson et al., teaches the use of 2,6-dinitro-p-cresol as a polymerization inhibitor of vinyl aromatic compounds. U.S. Pat. No. 4,466,905, Butler et al., teaches that a combination of 2,6-dinitro-p-cresol and p-phenylenediamine compounds will inhibit polymerization in distillation columns when oxygen is present. U.S. Pat. No. 4,774,374, Abruscato et al., teaches compositions and processes for inhibiting the polymerization of a vinyl aromatic monomer employing the oxygenated reaction product of oxygen and N-aryl-N'-alkyl-p-phenylenediamine compound.

U.S. 4,720,566, Martin, teaches methods and compositions of a hydroxylamine compound and a phenylenediamine compound used for inhibiting the polymerization of acrylonitrile in a quench tower. This system differs from a vinyl aromatic purification process in the type of monomer involved, but also in that oxygen is readily present in an acrylonitrile quench column, the quench tower reactor effluent is cooled by contact with a recirculating water stream and sulfuric acid is added to the quench column.

While these uses may inhibit vinyl aromatic monomer polymerization, it would be advantageous to possess polymerization inhibitors that avoid the use of highly toxic compounds such as dinitrophenol compounds and function in an oxygen-free environment.

DETAILED DESCRIPTION OF THE INVENTION

The present invention relates to methods for inhibiting the polymerization of vinyl aromatic monomer compounds under processing conditions comprising adding to said monomer an inhibitor composition comprising a hydroxylamine compound and a phenylenediamine compound.

The methods of the present invention prove efficacious at inhibiting the polymerization of vinyl aromatic monomers, particularly styrene, during their processing. These processing conditions include but are not limited to purification and distillation of vinyl aromatic monomers.

The hydroxylamine compounds useful in this invention generally have the formula:

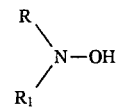

wherein R and $R_1$ are the same or different and are hydrogen, alkyl, aralkyl, or hydroxyalkyl groups and preferably have about 3 to about 20 carbon atoms, except when R is H, then $R_1$ is a $C_6$ to $C_{20}$ alkyl group. The preferred hydroxylamine compounds are N,N'-diethylhydroxylamine (DEHA) and isopropylhydroxylamine (IPHA).

The phenylenediamine compounds useful in this invention generally have the formula:

wherein $R_2$, $R_3$, $R_4$, and $R_5$ are the same or different and are hydrogen, alkyl, aryl, alkaryl or aralkyl groups having from 1 to about 20 carbons. The preferred phenylenediamine compound is N,N'-di-sec-butyl-phenylenediamine (PDA).

The methods of the present invention prove effective at inhibiting the polymerization of vinyl aromatic monomers during oxygen free processing. The phrase "oxygen-free processing conditions" is meant to define the substantially oxygen-free conditions under which vinyl aromatic monomers, particularly styrene are processed. These conditions, exemplified by but not limited to distillation and purification processes, generally have less than 2 parts per million parts oxygen present and preferably less than one part per million parts oxygen present. Pure styrene saturated with air at room temperature contains about 60 parts per million of dissolved oxygen.

The total amount of hydroxylamine compound and phenylenediamine compound used in the methods of the present invention is that amount which is sufficient to inhibit polymerization and will vary according to the conditions under which the vinyl aromatic monomer is being processed and exposed to high temperatures. At higher temperatures and higher monomer contamination, larger amounts of the polymerization inhibiting composition are required.

Preferably, the total amount of polymerization inhibiting composition added to the vinyl aromatic monomer ranges from a total of 1 to about 10,000 parts per million pads of monomer. More preferably, the range is about 5 parts to about 500 parts of the composition per million parts of monomer.

The weight ratio of hydroxylamine compound to phenylenediamine compound ranges from 1:9 to 9:1 with a weight ratio of 1:1 preferred.

The compositions of the present invention can be added to the vinyl aromatic monomer by any conventional method, either as individual components or as a combination. It is preferred that the individual ingredients are added to the monomer as a single treatment.

The combination of the present invention may be added to the vinyl aromatic monomer as either a dispersion or as a solution using a suitable liquid carrier or solvent. Any solvent that is compatible with the individual ingredients of the composition and the vinyl aromatic monomer may be employed.

Accordingly, it is possible therefor to produce a more effective vinyl aromatic monomer polymerization inhibition treatment than is obtainable by the use of any one ingredient alone when measured at comparable treatment levels. This enhanced activity allows for the concentration of each of these ingredients to be lowered and the total quantity of polymerization inhibitor required, particularly at higher processing temperatures, may be reduced.

This invention will now be further described with reference to a number of specific examples which are to be regarded solely as illustrative and not as restricting the scope of the invention.

Examples

In order to evaluate the improved polymerization inhibition of the inventive combinations and to demonstrate the enhanced activity of the combination, styrene polymerization testing was performed.

Uninhibited styrene (5 ml) was placed in a test tube and the appropriate amount of treatment was added. The tube was capped with a septum and argon was bubbled through the liquid at 15 ml/min for 3 minutes. Then, the tubes were placed in an oil bath heated to 100° C. for 2 hours. The amount of polystyrene formed was determined by methanol precipitation. Results of this testing are summarized in Table I.

TABLE I

| Treatment | Styrene Polymerization Test Uninhibited styrene at 100° C. | |
|---|---|---|
| | Dose(ppm) | Polymer formed (mg/5 ml) |
| Blank | — | 271 |
| IPHA | 25 | 232 |
| IPHA | 50 | 150 |
| IPHA | 100 | 96 |
| IPHA/PDA | 25/25 | 89 |
| IPHA/PDA | 50/50 | 38 |
| Blank | — | 239 |
| DEHA | 25 | 192 |
| DEHA | 50 | 149 |
| DEHA | 100 | 98 |
| DEHA/PDA | 25/25 | 94 |
| DEHA/PDA | 50/50 | 54 |
| PDA | 100 | 86 |

IPHA is isopropylhydroxylamine
DEHA is N,N'-diethylhydroxylamine
PDA is N,N'-di-sec-butyl-p-phenylenediamine The results of this testing indicate that the composition of hydroxylamine compound and phenylenediamine compound, particularly IPHA/ PDA and DEHA/PDA, provides enhanced activity over either hydroxylamine compound at inhibiting the polymerization of styrene. These results are particularly indicative of the compositions enhanced activity at inhibiting the polymerization of styrene under oxygen free conditions and high temperatures which are present when styrenic is undergoing processing such as distillation or purification.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what we claim is:

1. A method for inhibiting the polymerization of vinyl aromatic monomers in an oxygen-free vinyl aromatic monomer processing system comprising adding an effective polymerization inhibiting amount of a combination of a hydroxylamine compound and a phenylenediamine compound.

2. The method as claimed in claim 1 wherein said hydroxylamine compound has the formula:

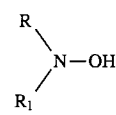

wherein R and $R_1$ are the same or different and are hydrogen, alkyl, aralkyl, or hydroxyalkyl groups and preferably have about 3 to about 20 carbon atoms.

3. The method as claimed in claim 2 wherein said hydroxylamine compound is N,N'-diethylhydroxylamine.

4. The method as claimed in claim 2 wherein said hydroxylamine compound is isopropylhydroxylamine.

5. The method as claimed in claim 1 wherein said phenylenediamine compound has the formula:

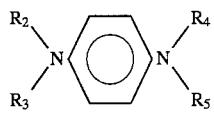

wherein $R_2$, $R_3$, $R_4$ and $R_5$ are the same or different and are hydrogen, alkyl, aryl, alkaryl, or aralkyl groups having from 1 to about 20 carbon atoms.

6. The methods as claimed in claim 5 wherein said phenylenediamine compound is N,N'-di-sec-butyl-p-phenylenediamine.

7. The method as claimed in claim 1 wherein said combination is added to said vinyl aromatic monomer in an amount ranging from 1 part to about 10,000 parts per million parts vinyl aromatic monomer.

8. The method as claimed in claim 1 wherein said vinyl aromatic monomer is styrene.

* * * * *